(12) United States Patent
Kim et al.

(10) Patent No.: US 8,691,749 B2
(45) Date of Patent: Apr. 8, 2014

(54) PEPTIDE AND USE THEREOF

(75) Inventors: Hae Jin Kim, Daejeon (KR); Eun Joung Moon, Daejeon (KR); Yang Seon Kim, Daejeon (KR); Young Joon Kwon, Daejeon (KR)

(73) Assignee: Ensoltek Co., Ltd., Daejeon (KR)

( * ) Notice: Subject to any disclaimer, the term of this patent is extended or adjusted under 35 U.S.C. 154(b) by 0 days.

(21) Appl. No.: 13/389,051

(22) PCT Filed: Feb. 12, 2010

(86) PCT No.: PCT/KR2010/000907
§ 371 (c)(1),
(2), (4) Date: Feb. 6, 2012

(87) PCT Pub. No.: WO2011/019123
PCT Pub. Date: Feb. 17, 2011

(65) Prior Publication Data
US 2012/0190625 A1    Jul. 26, 2012

(30) Foreign Application Priority Data

Aug. 14, 2009   (KR) .................. 10-2009-0075142

(51) Int. Cl.
*A61K 38/00* (2006.01)
*A61P 35/00* (2006.01)
*A61K 38/08* (2006.01)

(52) U.S. Cl.
USPC ................... 514/1.1; 514/19.3; 514/21.7

(58) Field of Classification Search
None
See application file for complete search history.

(56) References Cited

U.S. PATENT DOCUMENTS

| 6,277,812 | B1 | 8/2001 | Ruoslahti et al. | |
| 6,509,314 | B1* | 1/2003 | Ruoslahti et al. | 514/9.4 |
| 2003/0203834 | A1* | 10/2003 | Tallant et al. | 514/1 |
| 2004/0031072 | A1* | 2/2004 | La Rosa et al. | 800/278 |
| 2005/0059580 | A1* | 3/2005 | Fallon et al. | 514/8 |
| 2007/0014767 | A1 | 1/2007 | Saenz et al. | |
| 2008/0107705 | A1* | 5/2008 | McDermott | 424/423 |

FOREIGN PATENT DOCUMENTS

| JP | 07-504886 A | 6/1995 |
| WO | 03/015615 A3 | 2/2003 |
| WO | 2008/054764 A2 | 5/2008 |
| WO | 2009/002472 A1 | 12/2008 |

OTHER PUBLICATIONS

Ahn, SH et al., Spine 27, 911-917, 2002.
Burke JG et al., Spine 28, 2685-2693, 2003.
Kang JD et al., Spine 21, 271-277, 1996.
Weiler C et al., Spine 30, 44-54, 2005.
Igarashi T et al., Spine 25, 2975-2980, 2000.
Olmarker K et al., Spine 23, 2538-2544, 1998.
Le Maitre CL et al., Arthritis Res Ther7, R732-R745, 2005.
Seguin CA et al., Spine 30, 1940-1948, 2005.
Masuda K et al., Spine 31, 742-754, 2006.
Imai Y et al., Spine 32, 1197-1205, 2007.
Zhang Y et al., Spine 33, 831-838, 2008.
Prud'homme GJ, Lab Invest87, 1077-1091, 2007.
Lu et al., Spine 22, 1828-34, 1997.
Park TJ.et al., MolCarcinog 47, 784-796, 2008.
Gressner AM. et al., J Hepatol 26, 1079-1092, 1997.
GenBank AAG40163.1 in NCBI database 'biglycan-like protein 2[Petromyzonmarinus], Dec. 14, 2000.
BegonaSantiage et al., J. Invest. Dermatol., vol. 125, No. 3, pp. 450-455, 2005.
Kotaro Noshida et al., Spine, vol. 24(23), pp. 2419-2425, 1999.
Ann M. Kapoun et al., Circ. Res., vol. 94(4), pp. 453-461, 2004.
GenBank BAD97022 in NCBI database 'biglycanpreproprotein variant [*Homo sapiens*]', Apr. 29, 2009.
Seikou Shintani, et al. "Biglycan-Like Exracellular Matrix Genes of Agnathans and Teleosts," Journal of Molecular Evolution (2000) 51, pp. 363-373.
Nerlich, Andreas G., et al. "Expression of fibronectin and TGF-b1 mRNA and protein suggest altered regulation of extracellular matrix in degenerated disc tissue." Eur Spine J (2005) 14: 17-26. Published online Sep. 1, 2004.
Database UniProtKB Accession No. Q865A8 (Q865A8_HORSE). available at http://www.uniprot.org/uniprot/Q865A8, Nov. 13, 2013.
Kapoun, Ann M., et al. "B-Type Natriuretic Peptide Exerts Broad Functional Opposition to Transforming Growth Factor-b in Primary Human Cardiac Fibroblasts: Fibrosis, Myofibroblast Conversion, Proliferation, and Inflammation." Circulation Research: Journal of the American Heart Association. originally published online Jan. 15, 2004.
Santiago, Begona, et al. "Topical Application of a Peptide Inhibitor of Transforming Growth Factor-b1 Ameliorates Bleomycin-Induced Skin Fibrosis." J. Invst Dermatol 125:450-455, 2005.
Prud'Homme, Gerald J., et al. "Pathobiology of transforming growth factor b in cancer, fibrosis and immunologic disease, and therapeutic considerations." Laboratory Investigation (2007) 87, 1077-1091.

* cited by examiner

*Primary Examiner* — Cecilia J Tsang
*Assistant Examiner* — Sergio Coffa
(74) *Attorney, Agent, or Firm* — Novick, Kim & Lee, PLLC; Jae Youn Kim

(57) ABSTRACT

The present invention provides a peptide comprising an amino acid sequence of SEQ ID NO: 1 and a pharmaceutically acceptable salt thereof effective for treating degenerative disc diseases, treating body organ fibrosis, treating cancer and/or treating glomerulosclerosis, and effective for the inhibition of TGF-beta 1 signaling.

6 Claims, 3 Drawing Sheets

PEPTIDE AND USE THEREOF

CROSS REFERENCE TO RELATED APPLICATIONS

The present application is a 35 U.S.C. 371 National Phase Entry Application from PCT/KR2010/000907, filed Feb. 12, 2010, and designating the United States, which claims the benefit of the Korean Patent Application No. 10-2009-0075142, filed Aug. 14, 2009, which is incorporated herein its entirety and for all purposes.

REFERENCE TO SEQUENCE LISTING

This application contains a Sequence Listing submitted as an electronic text file named "P09062-ENS_sequence.txt" created on Oct. 15, 2009, and having a size of 424 bytes. The information contained in this electronic file is hereby incorporated by reference in its entirety pursuant to 37 CFR §1.52 (e)(5).

TECHNICAL FIELD

The present invention relates to a novel peptide which is effective for treating and/or preventing degenerative disc diseases, treating body organ fibrosis, treating cancer, treating glomerulosclerosis, or the like.

BACKGROUND ART

Degenerative disc disease (DDD), a cause of chronic lower back pain, is a pathological condition which is accompanied by lower back pain resulting from cracking and cleavage of a disc due to disc degeneration or disc height reduction in response to dehydration of the disc (particularly in nucleus pulposus) with aging. Degenerated disc is characterized by increased abnormal nerve and angiogenesis, and changes in the number and function of cells (cluster formation, necrosis, apoptosis, etc.). One of molecular characteristics of degenerated disc is a decrease of aggrecan. The loss of aggrecan, which plays a crucial role on the disc's load-bearing, results in a drop of disc osmotic pressure, thus being capable of no longer retaining water, which consequently accelerates the existing disc degeneration including the existing annulus fibrosus, and has significant influence on other spinal structures and functions, such as degeneration and hypertrophy of facet joint and ligamentum flavum.

As currently available therapies for pathological chronic lower back pain including these degenerative disc diseases, there are medical therapies including analgesic, exercise rehabilitation therapies, and the like. Unfortunately, these therapeutic approaches suffer from a frequent relapse of the disease, a need for a long period of time and great efforts to treat the concerned disease, and also risk of possible complications due to prolonged medication.

When there is no favorable outcome of the illness even after treatment with such long-term conservative therapy, the patient will inevitably receive surgical therapy. Representative surgical treatments include conventional lumbar fusion surgery involving complete removal of the affected disc tissues and bone graft insertion to the target lesion site, and the recently devised artificial disc insertion. However, these surgical methods have various disadvantages such as being relatively expensive and also potential risk of early and late surgical complications arising from surgery. For example, the lumbar fusion surgery frequently requires periodic redo surgery due to degeneration of adjacent discs. An artificial disc developed to reduce this disadvantage does not provide satisfactory results of long-term follow-up study. So the artificial disc surgery is not commonly performed nowadays. As described above, there is a great difficulty in treating chronic lower back pain due to degenerative disc diseases. To cope with such situations, as an alternative approach to the conservative therapy and surgical therapy, a variety of experimental therapies have been attempted to achieve disc regeneration while minimizing degeneration of the disc itself.

In recent years, there have been tried several biological therapies for treating disc degeneration, e.g., a method which up-regulates the production of important matrix proteins (for example, aggrecan), a method which down-regulates the catabolism induced by pro-inflammatory cytokines (for example, interleukin-1 (IL-1), tumor necrosis factor-alpha (TNF-α)) (Ahn, S H et al., *Spine* 27:911-917, 2002; Burke J G et al., *Spine* 28:2685-2693, 2003; Kang J D et al., *Spine* 21:271-277, 1996; Weiler C et al., *Spine* 30:44-53, 2005; Igarashi T et al., *Spine* 25:2975-2980, 2000; Olmarker K et al., *Spine* 23:2538-2544, 1998; Le Maitre C L et al., *Arthritis Res Ther* 7:R732R745, 2005; and Seguin C A et al., *Spine* 30:1940-1948, 2005).

These biological therapeutic methods have been performed largely outside the country. The popular method attracting a great deal of interest is direct injection of a bone growth factor (Bone morphogenic protein, BMP) into a disc or transplantation of therapeutic gene-injected disc cells (Masuda K et al., *Spine* 31:742-745, 2006; Imai Y et al., *Spine* 32:1197-1205, 2007; Zhang Y et al., *Spine* 33:831-838, 2008). However, this method is merely a method of achieving physical changes of a disc structure through physical regeneration, which does not provide relief or removal of pain in patients, and a disc overgrowth, if any, may result in aggravation of neurological conditions due to nerve compression.

Meanwhile, it is known that TGF-beta1 signaling is involved in fibrosis, apoptosis, angiogenesis, tumor cell invasion and metastasis, and the inhibition of TGF-beta1 signaling may be a feasible measure to make treatment of body organ fibrosis, cancer, and/or glomerulosclerosis (Prud'homme G J, *Lab Invest* 87:1077-1091, 2007).

To this end, there is a need for the development of a new biological material which is effective for degenerative disc disease by promoting disc regeneration while minimizing degeneration of the disc itself, and is capable of treating body organ fibrosis, cancer, glomerulosclerosis, or the like, through the inhibition of TGF-beta1 signaling.

DISCLOSURE OF THE INVENTION

Technical Problem

The present invention is intended to provide a novel peptide, which is capable of promoting disc regeneration while minimizing degeneration of the disc itself.

Further, the present invention is intended to provide an effective composition for treating body organ fibrosis, cancer, or glomerulosclerosis.

Technical Solution

The present invention provides a peptide comprising an amino acid sequence (LQVVYLH) of SEQ ID NO: 1 or a variant, or pharmaceutically acceptable salt thereof.

In the amino acid sequence of SEQ ID NO: 1, L, Q, V, Y, and H represent leucine (Leu), glutamine (Gln), valine (Val), tyrosine (Tyr), and histidine (His), respectively.

Each of constituent amino acids of the peptide may in the L-form, D-form, and/or DL-form, all of which are encompassed in the constituent amino acids of the peptide of the present invention.

The variant is a form in which a structure of the peptide of the present invention is partially altered by spontaneous variation or artificial variation while not causing any change of the main activity. For example, it may be one wherein one or more of amino acids at the position of glutamine, tyrosine and histidine in the amino acid sequence of SEQ ID NO: 1 are substituted with other amino acids. Preferred is one wherein substitutions of glutamine with asparagine, tyrosine with phenylalanine or tryptophan, and/or histidine with lysine or arginine are introduced in the amino acid sequence of SEQ ID NO: 1. Glutamine and asparagine belong to the group of amino acids containing terminal amide group. Tyrosine, phenylalanine and tryptophan belong to the group of aromatic amino acids containing aromatic side chains. Histidine, lysine and arginine belong to the group of basic amino acids containing very polar side chain, which render them highly hydrophilic. It is regarded that amino acids in the same group have the same or similar biochemical characteristics (size, shape, charge, hydrogen-bonding capacity, or chemical reactivity).

The peptide or the variant thereof may have the general formula (I)

$$L\text{-}X_1\text{-}VV\text{-}X_2\text{-}L\text{-}X_3 \qquad (I),$$

wherein $X_1$ is Q or N; $X_2$ is Y, F, or W; $X_3$ is H, K, or R; L is Leucine; Q is Glutamine N is Asparagine V is Valine Y is Tyrosine F is Phenylalanine W is Tryptophan H is Histidine K is Lysine and R is Arginine.

Examples of the pharmaceutically acceptable salt may include hydrochloride, sulfate, phosphate, lactate, maleate, fumarate, oxalate, methanesulfonate, p-toluenesulfonate, and the like.

Further, the present invention provides a medicinal use of a peptide or a variant, or pharmaceutically acceptable salt thereof of the present invention. The medicinal use includes therapeutic and/or preventive use for degenerative disc diseases, therapeutic use for body organ fibrosis, therapeutic use for cancer, and therapeutic use for glomerulosclerosis. The treatment of body organ fibrosis, cancer, or glomerulosclerosis is by the inhibition of Transforming Growth Factor-beta1 (TGF-β1) signaling.

TGF-β is known as a highly pleiotropic cytokine that plays an important role in apoptosis control, angiogenesis, wound healing, immune regulation, and tumor biology. TGF-β exists in three isoforms: TGF-β1, TGF-β2, and TGF-β3. All three TGF-βs use the same receptor. The TGF-β receptor has three components: type I (RI or ALK5), type II (RII), and type III (RIII or betaglycan). TGF-β (all isoforms) binds RIII and recruits RII, which then phosphorylates RI to form a heterotetrameric serine/threonine kinase complex. In turn, RI phosphorylates Smad2 and Smad3 (receptor-associated Smads (R-Smads)), and the latter form a heteromeric complex with Smad4, which translocates to the nucleus, binds to DNA and regulates transcription (Prud'homme G J, Lab Invest 87:1077-1091, 2007).

As used herein, the term "inhibition of TGF-beta1 signaling" means that TGF-β1 fails to bind to the receptor, then Smad2 and Smad3 fail to undergo phosphorylation, thus failing to form a complex with Smad4, and as a result, the complex fails to translocate to the nucleus and regulate transcription.

Accordingly, the present invention provides a composition for treating and/or preventing a degenerative disc disease, comprising a peptide or a variant or pharmaceutically acceptable salt thereof of the present invention.

Further, the present invention provides a composition for treating body organ fibrosis, comprising a peptide or a variant or pharmaceutically acceptable salt thereof of the present invention.

Further, the present invention provides a composition for treating cancer, comprising a peptide or a variant or pharmaceutically acceptable salt thereof of the present invention.

Further, the present invention provides a composition for treating glomerulosclerosis, comprising a peptide or a variant or pharmaceutically acceptable salt thereof of the present invention.

The peptide of the present invention can be prepared by processes commonly used in peptide synthesis. For example, the peptide can be prepared by those processes described in Schroder and Lubke, The Peptides, Vol. 1, Academic Press, New York, 1965, and the like, and can be prepared by either solution-phase synthesis or solid-phase synthesis.

Examples of the methods for formation of the peptide bonds include azide method, acid chloride method, symmetrical anhydride method, mixed anhydride method, carbodiimide method, carbodiimide-additive method, activated ester method, carbodiimidazole method, oxidation-reduction method, and the method employing Woodward reagent K. In the synthesis of peptide, the cystine moiety can be formed by employing a cystine derivative or by converting a cysteine moiety of the peptide chain into a cystine moiety after the formation of the peptide chain, by the conventional method.

Before carrying out the coupling reaction, a carboxyl group, amino group, guanidino group, hydroxyl group, and the like which do not participate in the reaction can be protected, and the carboxyl group and amino group which participate in the coupling reaction can be activated by methods known in the art.

Examples of the protecting groups for the carboxyl group may include ester-forming groups such as methyl, ethyl, benzyl, p-nitrobenzyl, t-butyl and cyclohexyl.

Examples of the protecting groups for the amino group may include benzyloxycarbonyl, t-butoxycarbonyl, isobornyloxycarbonyl, and/or 9-fluorenylmethyloxycarbonyl.

Examples of the protecting groups for the guanidino group may include nitro, benzyloxycarbonyl, tosyl, p-methoxybenzenesulfonyl and/or 4-methoxy-2,3,6-trimethylbenzenesulfonyl.

Examples of the protecting groups for the hydroxyl group may include t-butyl, benzyl, tetrahydropyranyl and/or acetyl.

Examples of the activated forms of carboxyl group may include symmetrical anhydride, azide and active ester (ester with alcohol, e.g., pentachlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide and 1-hydroxybenzotriazole).

An example of the activated amino group is amide phosphate.

The reaction is carried out in a solvent such as chloroform, dichloromethane, ethyl acetate, N,N-dimethylformamide, dimethylsulfoxide, pyridine, dioxane, tetrahydrofuran, water, methanol or a mixture thereof.

The reaction temperature may be in the range of approx. −30 to 50° C., which is generally employed for the reaction.

The reaction for removing the protecting group of the peptide of the present invention may differ depending on the kind of the protecting group, but it should be the one, which is able to release the protecting group without giving any influence to the peptide bonding.

The protecting group can be removed by acid treatment, for example, treatment with hydrogen chloride, hydrogen bromide, hydrogen fluoride, methanesulfonic acid, trifluoromethanesulfonic acid, trifluoroacetic acid or a mixture of these acids. Further, reduction with a sodium metal in liquid ammonia or catalytic reduction over palladium-carbon can be employed.

In performing the reaction for removing the protecting group by the above acid treatment, an additive such as anisole, phenol or thioanisole may be adopted.

After the reaction is completed, the prepared peptide of the present invention can be recovered by a conventional process for purification of peptides, for example, extraction, partition, reprecipitation, recrystallization or column chromatography.

Further, the peptide of the present invention can be converted into its variant or its pharmaceutically acceptable salt as described above in the conventional manner.

The peptide in accordance with the present invention may be synthesized by an automated peptide synthesizer or may be produced by genetic engineering techniques. For example, a desired peptide can be produced by preparing a fusion gene encoding a fusion protein consisting of a fusion partner and the peptide of the present invention through gene manipulation, transforming a host microorganism with the fusion gene, expressing a desired peptide in the form of a fusion protein in the host microorganism, and cleaving and separating the peptide of the present invention from the fusion protein using a protease or compound.

The amino acids used in the present invention are abbreviated according to the IUPAC_IUB nomenclature as below.

| Amino acid | Abbreviation |
|---|---|
| Alanine | A |
| Arginine | R |
| Asparagine | N |
| Aspartic acid | E |
| Cysteine | C |
| Glutamic acid | D |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

A dose of the peptide or a variant or pharmaceutically acceptable salt thereof is in the range of 50 µg/day to 1 mg/day, preferably 0.5 mg/day to 1 mg/day for parenteral administration. For oral administration, the dose is 1.2 to 1.5 times larger than the parenteral dose. For rectal administration, the dose is 2 to 5 times larger than the parenteral dose. The peptide of the present invention is administered largely by parenteral routes, for example local injection (intradiscal injection for degenerative disc disease, and local intralesional injection for other body organ fibrosis and cancer), intravenous/intramuscular or subcutaneous injection, intracerebroventricular or intraspinal administration or transnasal administration and intrarectal administration. Further, oral administration may be adopted, if necessary.

The peptide or composition of the present invention, in combination with a pharmaceutically acceptable carrier, can be formulated into desired dosage forms such as injections, suppositories, powders, nasal drops, granules, tablets, etc.

The pharmaceutically acceptable carrier can be prepared according to a number of factors well-known to those skilled in the art, for example, taking into consideration the following non-limiting factors: the particular physiologically active material to be used, and its concentration, stability and intended bioavailability; the disease, disorder or condition being treated; the subject being treated, and its age, size and general condition; and the composition's intended route of administration, for example nasal, oral, ocular, local, transdermal, and intramuscular. Generally, examples of the pharmaceutically acceptable carrier used for the administration of a physiologically active material, other than the oral administration route, may include D5W (5% glucose in water), an aqueous solution containing 5% by volume or less of dextrose, and physiological saline. In the case of local intralesional injection, a variety of injectable hydrogels may be employed to enhance therapeutic effects and increase the duration of drug efficacy. In addition, the pharmaceutically available carrier may contain additional ingredients that can enhance the stability of active ingredients, such as preservatives and antioxidants. The peptide or composition of the present invention may be preferably formulated into a desired dosage form, depending upon diseases to be treated and ingredients, using any appropriate method known in the art, for example, as disclosed in "Remington's Pharmaceutical Sciences," Mack Publishing Co., Easton, Pa. (latest edition).

The peptide of the present invention can be stored in a physiological saline solution and can be freeze-dried in an ampoule after addition of mannitol or sorbitol. The freeze-dried peptide may be dissolved in physiological saline or the like for reconstitution prior to use.

Further, the present invention provides a peptide or a variant or pharmaceutically acceptable salt thereof of the present invention for use as a medicament.

Further, the present invention provides a use of a peptide or a variant or pharmaceutically acceptable salt thereof of the present invention for the manufacture of a medicament for treating and/or preventing degenerative disc disease, body organ fibrosis, cancer, and/or glomerulosclerosis.

Further, the present invention provides a method for treating and/or preventing degenerative disc disease, body organ fibrosis, cancer, and/or glomerulosclerosis, comprising administering a peptide or a variant or pharmaceutically acceptable salt thereof of the present invention to a subject (a mammal including a human).

The treatment of body organ fibrosis, cancer, and/or glomerulosclerosis may be by the inhibition of TGF-beta1 signaling.

Advantageous Effects

A novel peptide of the present invention or a variant or pharmaceutically acceptable salt thereof is effective for treating and/or preventing degenerative disc diseases, body organ fibrosis, cancer, and/or glomerulosclerosis, and is effective for the inhibition of TGF-beta1 signaling.

MODE FOR INVENTION

Figure 1:
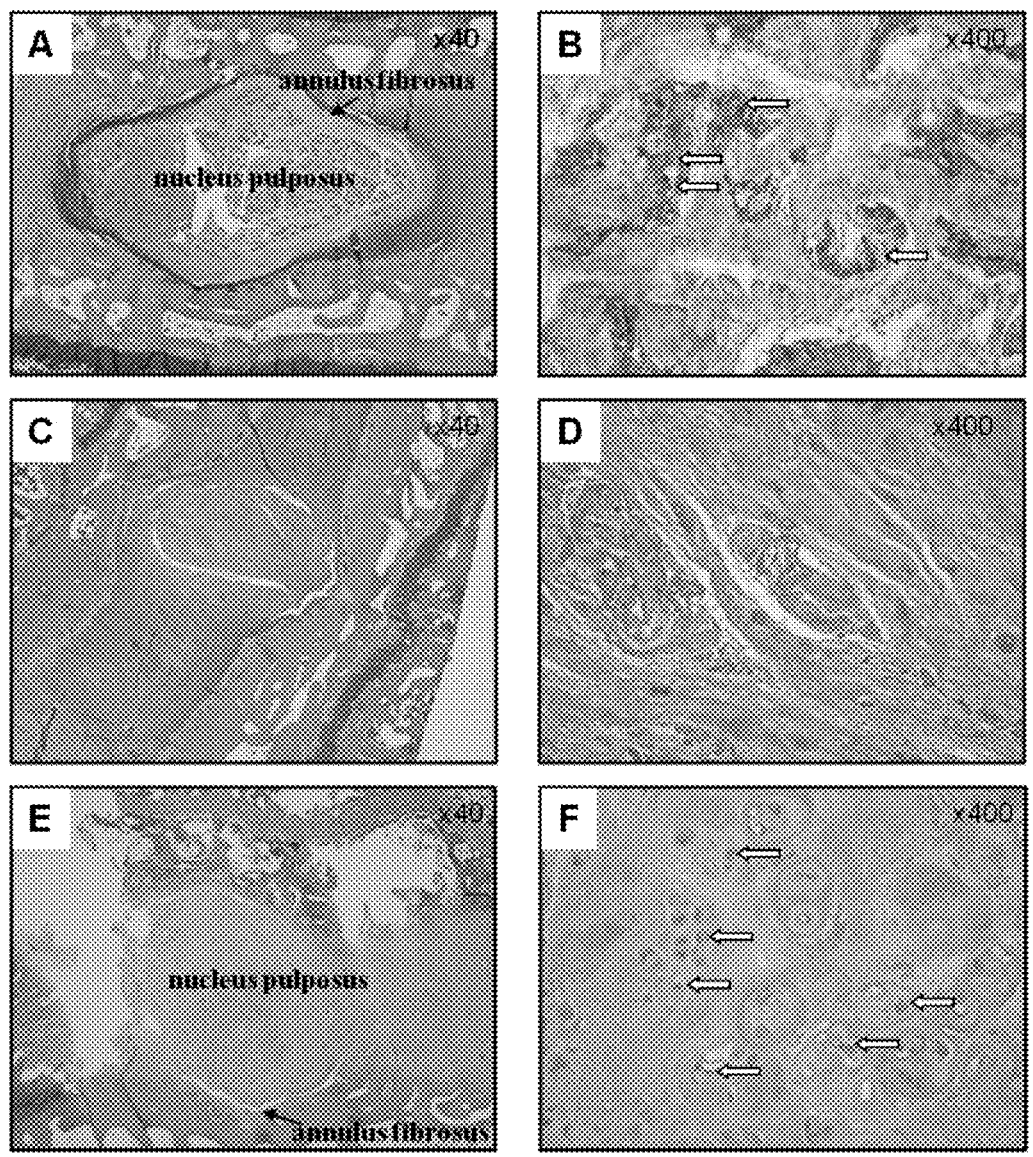
FIG. 1 illustrates a photograph taken after staining normal disc tissue, DMSO-administered degenerated disc tissue, and Example 1 peptide-administered degenerated disc tissue.

Now, the present invention will be described in more detail with reference to the following examples. These examples are provided only for illustrating the present invention and should not be construed as limiting the scope and spirit of the present invention.

Example 1

Preparation of Peptide

A peptide (LQVVYLH: SEQ ID NO: 1) having an amino acid sequence of SEQ ID NO: 1 was prepared by Peptron Inc. (Republic of Korea), at the request of the present inventors. Specifically, amino acid units were coupled one by one from the C-terminal, by Fmoc SPPS (9-fluorenylmethyloxycarbonyl solid phase peptide synthesis) using an automated peptide synthesizer (ASP48 S, Peptron Inc.).

$NH_2$-His(Trt)-2-chloro-Trityl Resin was used in which the first amino acid of the C-terminal of the peptide was attached to a resin. All the amino acids used in the peptide synthesis were those protected by Trityl (Trt), t-butyloxycarbonyl (Boc), t-butyl (t-Bu), and the like, whereby the N-terminal is protected by Fmoc, and residues are all removed in acid. As a coupling reagent, 2-(1H-benzotriazol-1-yl)-1,1,3,3-tetramethyluronium hexafluorophosphate (HBTU)/hydroxybenzotriazole (HOBt)/N-methylmorpholine (NMM) was used. (1) Protected amino acid (8 equivalents) and the coupling reagent HBTU (8 equivalents)/HOBt (8 equivalents)/NMM (16 equivalents) were dissolved in dimethylformamide (DMF) and added followed by reaction at room temperature for 2 hours. (2) The removal of Fmoc was carried out by adding 20% piperidine in DMF, followed by reaction at room temperature for 5 minutes twice. Reactions of (1) and (2) were repeated to prepare a basic peptide backbone, and the peptide was separated from the resin using trifluoroacetic acid (TFA)/1,2-ethanedithiol (EDT)/thioanisole/triisopropylsilane (TIS)/$H_2O$=90/2.5/2.5/2.5/2.5. The peptide was purified by reverse phase HPLC using a Vydac Everest C18 column (250 mm 22 mm, 10 μm), and then separated by water-acetonitrile linear gradient (10 to 75% (v/v) of acetonitrile) containing 0.1% (v/v) trifluoroacetic acid. A molecular weight of the purified peptide was confirmed using an LC/MS (Agilent HP1100 series), followed by freeze-drying.

Example 2

Confirmation of Disc Regeneration Effects

2-1. Preparation of Disc Degeneration Model Animal and Collection of Experimental Disc 30 rabbits (New Zealand white rabbits; Orient Bio Inc.), weighing 3 to 3.5 kg, were prepared irrespective of sex.

The rabbits were anesthetized by intramuscular injection of 5 mg/kg of xylazine (Rompun, Bayer) and 35 mg/kg of ketamine hydrochloride (Ketalar, Pfizer). Prior to the procedure, lateral plain X-ray using a fluoroscopic apparatus (Model VPX-200; Toshiba Co.) was obtained to establish the pre-injection baseline height of intervertebral disc. The baseline control refers to a standard for measurement of a disc space. After the rabbits were positioned on the laboratory table, L23, L34, L45, and L56 disc levels were confirmed by the machine, and annulus fibrosus was stabbed into the posterolateral side of the disc at L23, L45, and L56 levels, using an 18G needle. After recovery from the anesthesia, the animals were housed in a cage under the following breeding conditions: temperature 20-25° C., humidity 10%-50%, and Light/Dark (L/D) cycle: (light from 08:00 a.m. to 20:00 p.m.). All animals were fed once a day. X-ray photographs were taken 2 and 4 weeks after the initial annular puncture. The X-ray was taken after anesthesia. Based on the results of X-ray, an intervertebral disc height (IVD height) was measured. From the measurement results, disc degeneration degree was quantified by a modification of the method disclosed in Lu et al., *Spine.* 22:1828-34, 1997.

Thereafter, experiments were carried out for two separate groups, DMSO-administered control group and Example 1 peptide-administered experimental group, and the rabbits were euthanized by injection of ketamine (25 mg/kg) and sodium pentobarbital (1.2 g/kg, Nembutal, Ovation) according to the planned schedule, followed by extraction of the disc for histological and biochemical analysis, respectively.

2-2. Measurement of Disc Regeneration Effects by Disc Tissue Staining

Disc-degenerated rabbits from Section 2-1 were divided into two groups. Each group was given dimethyl sulfoxide (DMSO) and the peptide of Example 1 (0.5 mM/animal) by local intradiscal injection twice. The administration point for each group was 4 weeks after the induction of disc degeneration and 2 weeks thereafter. After the second administration, the animals were raised for 2, 4, and 8 weeks, respectively. At Weeks 4, 6, and 10 after the first administration of each of the Example 1 peptide and DMSO, the corresponding respective disc tissues were extracted and fixed in formalin. The fixed disc tissues were embedded in paraffin, and serial sections having a thickness of 4 m along the sagittal plane were prepared. Of these sections, two mid-sagittal sections were stained with hematoxylin and eosin (H&E). For the comparison with the normal disc tissue, the disc was extracted, treated and stained from the rabbits with no induction of disc degeneration according to the same method described above.

FIG. 1 illustrates the micrographic results of individual disc tissues, which were extracted and stained at Week 10. A and B: normal disc tissue, C and D: DMSO-administered degenerated disc tissue, and E and F: Example 1 peptide-administered degenerated disc tissue. A, C and E: ×40, and B, D and F: ×400. In the ×400 pictures, the arrow indicates a disc cell nucleus.

As a result, it was observed that the nucleus pulposus and the annulus fibrosus are definitely distinguishable therebetween and extracellular matrix components are abundant in the normal disc tissue (panels A and B of FIG. 1). In addition, distinctive staining of the cell nucleus was observed in the nucleus pulposus of the normal disc tissue (panel B of FIG. 1).

On the other hand, the DMSO-administered disc tissue exhibited a size reduction of disc, indefiniteness between the annulus fibrosus and the nucleus pulposus, and scarcity of extracellular matrix components (panels C and D of FIG. 1).

Further, it was difficult to find the stained cell nucleus in the nucleus pulposus region (panel D of FIG. 1). That is, these results indicate the death of cells, which had been present in the nucleus pulposus. The cell death due to disc degeneration is as already known, and the absence of cells resulted in no production of extracellular matrix components, thus further worsening disc degeneration.

The Example 1 peptide-administered disc tissue exhibited an increased size of disc as compared to the DMSO-administered disc tissue, being discernible between the nucleus pulposus and the annulus fibrosus, and abundance of extracellular matrix components (panels E and F of FIG. 1). In addition, vivid staining of the cell nuclei was observed in the nucleus pulposus region (panel F of FIG. 1).

From these results, it was demonstrated that the peptide of Example 1 has disc therapeutic effects by preventing a decrease of extracellular matrix components and death of cells due to disc degeneration.

Example 3

Confirmation of Increased Expression of Aggrecan Gene in Disc Tissues

Real-time PCR was carried out to examine a gene expression level of aggrecan, which is a representative extracellular matrix component in disc tissues.

In the same manner as in Example 2-1, animals were prepared and divided into two groups, to each of which DMSO and the peptide of Example 1 (0.5 mM/animal) were administered by local intradiscal injection. The administration point for each group was 4 weeks after the induction of disc degeneration and 2 weeks thereafter. After the second administration, the animals were raised for 2, 4, and 8 weeks, respectively. At Weeks 4, 6, and 10 after the first administration of each of the Example 1 peptide and DMSO, the corresponding respective disc tissues were extracted, and the nucleus pulposus and the annulus fibrosus were separated and placed in tubes, followed by quick-freezing in liquid nitrogen and storage in an ultra-low temperature freezer at −70° C.

Total RNA was isolated from the quick-frozen and stored disc tissue using a Trizol reagent (Invitrogen). cDNA was synthesized using the isolated total RNA (2 µg), oligo dT and MMLV-Reverse Transcriptase (Invitrogen).

The quantity of mRNA of GAPDH and aggrecan was examined by a Prism 7900HT (ABI) using PowerSYBR Green PCR Master Mix (Applied Biosystems Inc.). 25 ng of cDNA, 3 µl of 10 µM Primers, and 2× PowerSYBR Green PCR Master Mix were mixed to make a total volume of 10 µl. Real-time PCR was performed under the following reaction conditions: induction of enzymatic activity at 50° C. for 2 minutes and at 95° C. for 10 minutes, and then 45 cycles each consisting of reaction at 95° C. for 15 seconds and reaction at 60° C. for 1 minute, followed by measurement of each threshold cycle (CT) value. GAPDH was selected as a reference gene, and a CT value difference ($\Delta CT$) between the reference gene and the aggrecan gene was calculated. In addition, a CT value difference ($\Delta\Delta CT$) between the normal disc and the Example 1 peptide-administered disc (or DMSO-administered disc) was calculated. Then, $2^{(-\Delta\Delta CT)}$ was calculated and expressed in terms of percentage relative to the normal disc value.

Figure 2:
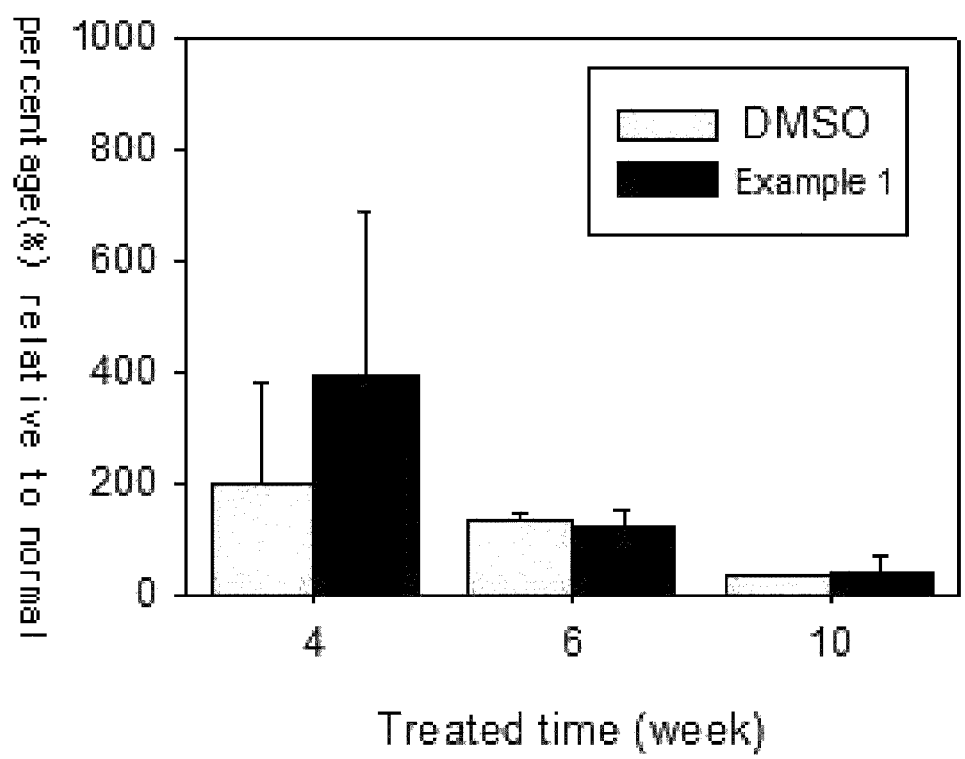
FIG. 2 illustrates a graph showing aggrecan gene expression levels of a DMSO-administered disc group and an Example 1 peptide-administered disc group in a disc degeneration model, in comparison with a normal disc group as a reference.

The results of real-time PCR are given in FIG. 2. FIG. 2 is a graph showing time-course aggrecan gene expression levels of the DMSO-administered disc group and the Example 1 peptide-administered disc group in the disc degeneration model, in comparison with a normal disc group as a reference. As shown in the above graph, it can be seen that at Week 4, the Example 1 peptide-administered disc tissue exhibited an increase in the aggrecan gene expression as compared to the DMSO-administered disc tissue. At Weeks 6 and 10, the Example 1 peptide-administered disc tissue exhibited an aggrecan expression level similar to that of the DMSO-administered disc tissue. Because the peptide of Example 1 was administered only at Weeks 0 and 2 and then the animals remained without further administration, it can be said that an increase in the expression of aggrecan gene at Week 4 was achieved by efficacy of the peptide of Example 1 which, however, did not maintain the aggrecan gene expression by Weeks 6 and 10. From these results, it can be seen that the peptide of the present invention exhibits disc regeneration effects by increasing the gene expression of aggrecan, a representative extracellular matrix component essential for disc regeneration in the disc tissue, and the duration of aggrecan gene expression-enhancing effects of the peptide is not excessively long to thereby exclude possible side effects due to an excessive increase of aggrecan gene expression.

Example 3

Confirmation of TGF-beta1 Signaling Inhibition

Inhibition of TGF-beta1 signaling by the peptide of Example 1 was confirmed in accordance with the following experimental method.

Treatment of HepG2 cells with TGF-beta1 is known to result in apoptosis, during which Smad2 is first phosphorylated (Park T J. et al., *Mol. Carcinog.* 47:784-796, 2008; and Gressner A M. et al., *J Hepatol.* 26:1079-1092, 1997). Using these properties, the experiment was carried out as follows. 1×10⁶ of HepG2 cells (ATCC; American Type Culture Collection) were seeded in a 60 mm dish, stabilized overnight, and then depleted of nutrients by serum-free media (SFM) for 24 hours. Prior to treatment of the cells with the peptide of Example 1, 5 ng/mL of TGF-beta1 (PromoKine, Germany) and the above peptide (1, 5, and 25 µM) were subjected to pre-incubation at 37° C. for 1 hour. Further, DMSO (2 µl/mL) was also pre-incubated with TGF-beta1 (5 ng/mL) at 37° C. for 1 hour. Then, the cells were treated with the pre-incubated solutions for 30 minutes, followed by extraction of proteins. In addition, the cells were previously treated only with 1004 of SB431542 (TOCRIS, USA), an inhibitor of the TGF-beta receptor, followed by incubation for 1 hour, and then treated with TGF-beta1 (5 ng/mL) for 30 minutes. Then, the cells were homogenized on ice in Radioimmunoprecipitation (RIPA) Lysis Buffer (Millipore) {50 mM Tris-HCl (pH 7.4), 150 mM NaCl, 0.25% deoxycholic acid, 1% NP-40, 1 mM ethylenediaminetetraacetic acid (EDTA), 1 mM phenylmethylsulfonyl fluoride (PMSF), 40 mM NaF, 1 mM $Na_3VO_4$, 1 mM dithiothreitol (DTT)}. The homogenate was sonicated five times using a BRANSON SONIFIER 450 with Output control 2.56, Duty cycle (%) 20, and Timer 6. The cell lysate was centrifuged at 4° C. and 12,000 rpm for 10 minutes, and the supernatant was used for Western blot analysis. The protein concentration was assayed using Bradford method. 30 µg of the protein was added to SDS sample buffer containing 2-mercaptoethanol. After allowing to stand at 95° C. for 5 minutes, fractionation was carried out by 10% SD S-PAGE, followed by Western blot. For Western blot analysis, the fractionated protein was transferred to a nitrocellulose membrane (Bio-Rad Lab), and blocked with 5% skim milk in PBS-T, followed by reaction with a 1:3000 dilution of the primary antibody in 5% skim milk in PBS-T, at 4° C. overnight. Next, the membrane was washed three times with PBS-T for 5 minutes, treated with a 1:5000 dilution of the horseradish peroxidase (HRP)-conjugated anti-rabbit secondary antibody (Bio-Rad Lab, 1706515) in 5% skim milk in PBS-T at room temperature for 1 hour, and subjected to color development using ECL (Amersham Pharmacia). Since Smad2 is first phosphorylated simultaneously with the binding of TGF-beta1 to the TGF-beta receptor, the phospho-Smad2 (ser465/467) antibody (Cell Signaling, 3101, 8) capable of detecting phosphorylated Smad2 was used as a primary antibody.

Figure 3:
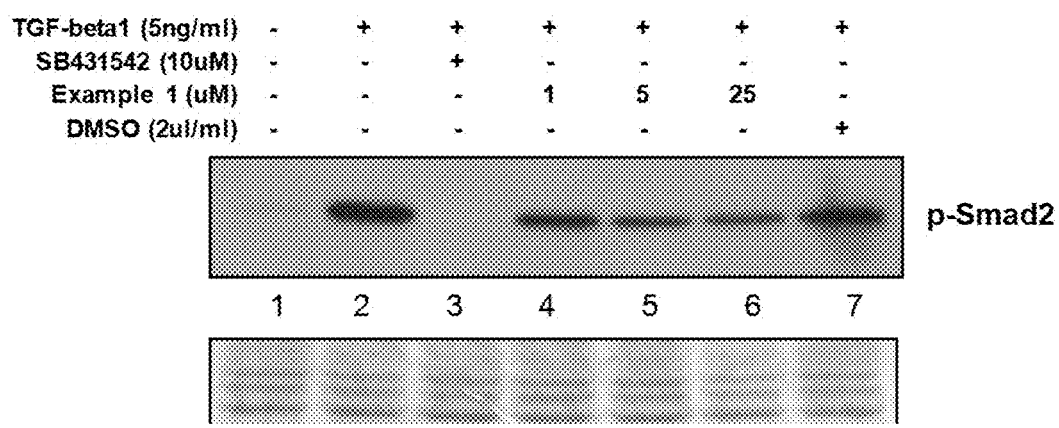
FIG. 3 illustrates the results of Western blot analysis for the confirmation of the phosphorylated Smad2 expressed in nontreated HepG2 cells, TGF-beta1-treated cells, TGF-beta1/SB431542-treated cells, TGF-beta1/Example 1 peptide-treated cells, and TGF-beta1/DMSO-treated cells.

The results are shown in FIG. 3. FIG. 3 illustrates the Western blot results (Lane 1: non-treated HepG2 cells, Lane 2: TGF-beta1-treated cells, Lane 3: TGF-beta1/SB431542-treated cells, Lanes 4, 5 and 6: cells treated with 1, 5, and 25 µM of peptide/TGF-beta1, respectively, and Lane 7: TGF-beta1/DMSO-treated cells). In FIG. 3, the symbol '+' represents that it was treated with the subject material, and '−' represents that it was not treated with the subject material. The bottom of FIG. 3 illustrates the Coomassie Blue staining results of the membrane used in Western blot, showing that the quantity of the protein is the same in all the lanes.

Referring to FIG. 3, it was observed that Lane 1 exhibits very little phosphorylation of the protein extracted from the non-treated HepG2 cells, whereas Lane 2 exhibits significant phosphorylation of the protein by TGF-beta1. In addition, it was observed that Lane 3 exhibits complete inhibition of phosphorylation by SB431542. It was confirmed that the phosphorylation degree of the protein was decreased in a dose-dependent manner, when the peptide of Example 1 was treated at a concentration of 1 µM, 5 µM, and 25 µM, respectively. DMSO-treated Lane 7 exhibited the same profiles as the treatment of TGF-beta1.

From these results, it can be seen that since the peptide of the present invention exhibits dose-dependent inhibition of TGF-beta1 signaling, diseases curable by the above-mentioned TGF-beta1 signaling inhibition, i.e., body organ fibrosis, cancer, and/or glomerulosclerosis can be treated (Prud'homme G J, Lab Invest 87:1077-1091, 2007). Further, it can be seen that the peptide of Example 1 does not completely inhibit TGF-beta1 signaling unlike SB431542. As TGF-beta1 signaling is an important regulatory mechanism in the human body, complete inhibition of TGF-beta1 signaling, such as by SB431542, may result in side effects. However, the peptide of the present invention decreases TGF-beta1 signaling in a dose-dependent manner, so the peptide concentration can be advantageously adjusted to thereby reduce possible side effects when it is used for the treatment of concerned diseases.

INDUSTRIAL APPLICABILITY

A novel peptide of the present invention or a variant or pharmaceutically acceptable salt thereof is effective for treating and/or preventing degenerative disc diseases, body organ fibrosis, cancer, and/or glomerulosclerosis, and is effective for the inhibition of TGF-beta1 signaling, and it is therefore industrially applicable.

What is claimed is:

1. A peptide consisting of an amino acid sequence of LQVVYLH (SEQ ID NO: 1), or pharmaceutically acceptable salt thereof.

2. A composition for treating degenerative disc disease, comprising the peptide of claim 1 or pharmaceutically acceptable salt thereof.

3. A composition for treating body organ fibrosis, cancer or glomerulosclerosis, comprising the peptide of claim 1 or pharmaceutically acceptable salt thereof.

4. The composition according to claim 3, wherein the treatment of body organ fibrosis, cancer or glomerulosclerosis is by the inhibition of TGF-beta1 signaling.

5. A method for treating a degenerative disc disease, comprising administering to a subject the peptide of claim 1 or pharmaceutically acceptable salt thereof.

6. A method for treating body organ fibrosis, cancer or glomerulosclerosis, comprising administering to a subject the peptide of claim 1 or pharmaceutically acceptable salt thereof.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthesized peptide

<400> SEQUENCE: 1

Leu Gln Val Val Tyr Leu His
1               5
```